(12) United States Patent
Lau et al.

(10) Patent No.: US 9,272,314 B2
(45) Date of Patent: Mar. 1, 2016

(54) DISHWASHER STEAM PURGE METHOD

(75) Inventors: Brooke L. Lau, Saint Joseph, MI (US);
Julio C. Moreira, Stevensville, MI (US);
Michelle L. Oakes, Flagstaff, AZ (US);
Ryan K. Roth, Saint Joseph, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 2037 days.

(21) Appl. No.: 12/339,666

(22) Filed: Dec. 19, 2008

(65) Prior Publication Data
US 2010/0154827 A1 Jun. 24, 2010

(51) Int. Cl.
| | | |
|---|---|---|
| B08B 9/00 | (2006.01) | |
| A47L 15/00 | (2006.01) | |
| A47L 15/42 | (2006.01) | |
| A61L 2/04 | (2006.01) | |
| B08B 9/08 | (2006.01) | |

(52) U.S. Cl.
CPC ............... *B08B 9/00* (2013.01); *A47L 15/0015* (2013.01); *A47L 15/4234* (2013.01); *A61L 2/04* (2013.01); *B08B 9/08* (2013.01); *A47L 15/4236* (2013.01); *A47L 2601/04* (2013.01); *A61L 2202/17* (2013.01)

(58) Field of Classification Search
None
See application file for complete search history.

(56) References Cited

U.S. PATENT DOCUMENTS

| | | |
|---|---|---|
| 3,049,450 A | 8/1962 | Koons et al. |
| 3,586,011 A | 6/1971 | Mazza |
| 4,246,916 A | 1/1981 | Fay et al. |
| 4,279,384 A | 7/1981 | Yamamoto |
| 4,366,005 A | 12/1982 | Oguri et al. |
| 6,422,180 B1 | 7/2002 | Yiu |
| 2004/0250837 A1* | 12/2004 | Watson et al. ............... 134/25.2 |

FOREIGN PATENT DOCUMENTS

| | | |
|---|---|---|
| DE | 4034380 A1 | 4/1992 |
| DE | 4233936 A1 | 4/1994 |
| DE | 102004048091 A1 | 4/2006 |
| EP | 0291713 A1 | 11/1988 |
| JP | 2002300995 A | 10/2002 |
| JP | 2006314667 A | 11/2006 |
| JP | 2007075249 A | 3/2007 |
| JP | 2007130143 A | 5/2007 |
| WO | 97/20493 A1 | 6/1997 |
| WO | 2004/023967 A1 | 3/2004 |
| WO | 2006/129963 A2 | 12/2006 |
| WO | 2006345928 A | 12/2006 |

* cited by examiner

*Primary Examiner* — Michael Kornakov
*Assistant Examiner* — Ryan Coleman

(57) ABSTRACT

A steam purge method for a dishwasher includes a washing cycle, a steam purge cycle and a rinse cycle. During the steam purge cycle, a dishwasher tub is filled with fluid to a level below a heating element in a wash chamber, heated and at least partially converted to steam in the wash chamber. After the steam purge cycle, the dishwasher is drained and the rinse cycle commences. Optionally, a heated drying cycle may be performed upon termination of the rinse cycle. A single heating element arranged in the wash chamber is utilized for heating washing fluid during each of washing, purging and steam generation cycles, as well as for the heated drying cycle.

19 Claims, 3 Drawing Sheets

US 9,272,314 B2

DISHWASHER STEAM PURGE METHOD

BACKGROUND OF THE INVENTION

1. Field of the Invention

The present invention pertains to the art of dishwashing and, more particularly, to a steam purge method for a dishwasher.

2. Description of the Related Art

Maintaining a high sanitation level in connection with the washing of dishes has been a long standing priority in commercial settings. However, the public has also become particularly concerned with minimizing the presence of germs in the home such that it is increasingly desirable to include sanitation options in domestic dishwashers. Typically, performing a sanitation operation in connection with a domestic dishwasher constitutes controlling a heating element during an overall washing cycle such that the washed dishware will be subject to high temperature washing, drying and sanitizing operations. To further enhance the degree to which dishware is cleaned, it has also been proposed to introduce steam into a dishwashing tub. Basically, steam has been utilized in dishwashers in order to aid in the removal of food debris from dishware. One such known dishwasher arrangement, as set forth in International Patent Application No. WO 2006/129963, incorporates a dedicated steam generator into the dishwasher, with the steam generator directing steam through pipes into a wash chamber containing the dishware.

Although the addition of steam can be advantageous, the requirement for additional components in a domestic dishwasher can add significantly to the manufacturing cost. In addition to the added component costs, the effectiveness of the added use of steam can greatly vary depending on both the manner in which the steam is provided and the time at which the steam is introduced in the overall washing cycle. Based on at least these reasons, it is considered desirable to effectively incorporate steam as part of an overall dishware cleaning strategy in a dishwasher, particularly in connection with a sanitation operation in a dishwasher, while avoiding the costs associated with the need for dedicated steam generating components.

SUMMARY OF THE INVENTION

The present invention is directed to a steam purge and sanitation method for a dishwasher. In general, the dishwasher includes a tub defining a wash chamber, a door movably mounted relative to the tub for selectively sealing the wash chamber, a heating element supported by the tub and exposed to the wash chamber, and a washing assembly for spraying washing fluid onto dishware within the wash chamber. The dishwasher also includes a control panel that allows a consumer to choose between numerous washing cycles and options, including a sanitizing option.

In accordance with the invention, it is desired to provide a steam cleaning operation as part of an overall dishwasher cycle, particularly when the sanitize option is selected. When the sanitize option is initiated, a main washing cycle is performed wherein washing fluid is introduced into the tub to a level substantially at or preferably above the heating element, the washing fluid is heated by activation of the heating element, and the heated washing fluid is distributed throughout the wash chamber via the washing assembly. Thereafter, the tub is drained. Preferably, the washing fluid has a minimum temperature of approximately 145° F. This washing cycle may be repeated multiple times depending on the type of washing cycle selected by the consumer. In accordance with the invention, after this washing cycle, a steam purge cycle is initiated, wherein the tub is partially filled with water to a level below the heating element, and the water is used to flush or purge the washing assembly. After purging, the heating element is activated and the purge water within the tub is heated to generate steam dispersed within the wash chamber. The heating element is deactivated after a predetermined period of time and allowed to cool before the tub is drained of the purge water. A disinfecting rinse cycle is then performed, wherein the tub is filled with rinse water to a level substantially at or preferably above the heating element, the rinse water is circulated by the washing assembly, heated by the heating element and utilized to rinse dishware within the wash chamber before a final drain event. Preferably, the rinse water has a minimum temperature of approximately 156° F. for sanitizing purposes. Thereafter, the heating element is again actuated to provide a drying heat to the dishware within the dishwasher.

With this arrangement, the same heating element effectively utilized for heating the washing fluid, heating rinse water, and drying the dishware is employed to generate the desired steam such that a very cost effective arrangement is established. In addition, by linking the steam generation with the wash system purging, the overall cycle time in not substantially increased and the steam is provided at an effective time in the overall dishwashing cycle. Additional objects, features and advantages of the present invention will become more readily apparent from the following detailed description of a preferred embodiment when taken in conjunction with the drawings wherein like reference numerals refer to corresponding parts in the several views.

DETAILED DESCRIPTION OF THE PREFERRED EMBODIMENT

Figure 1:
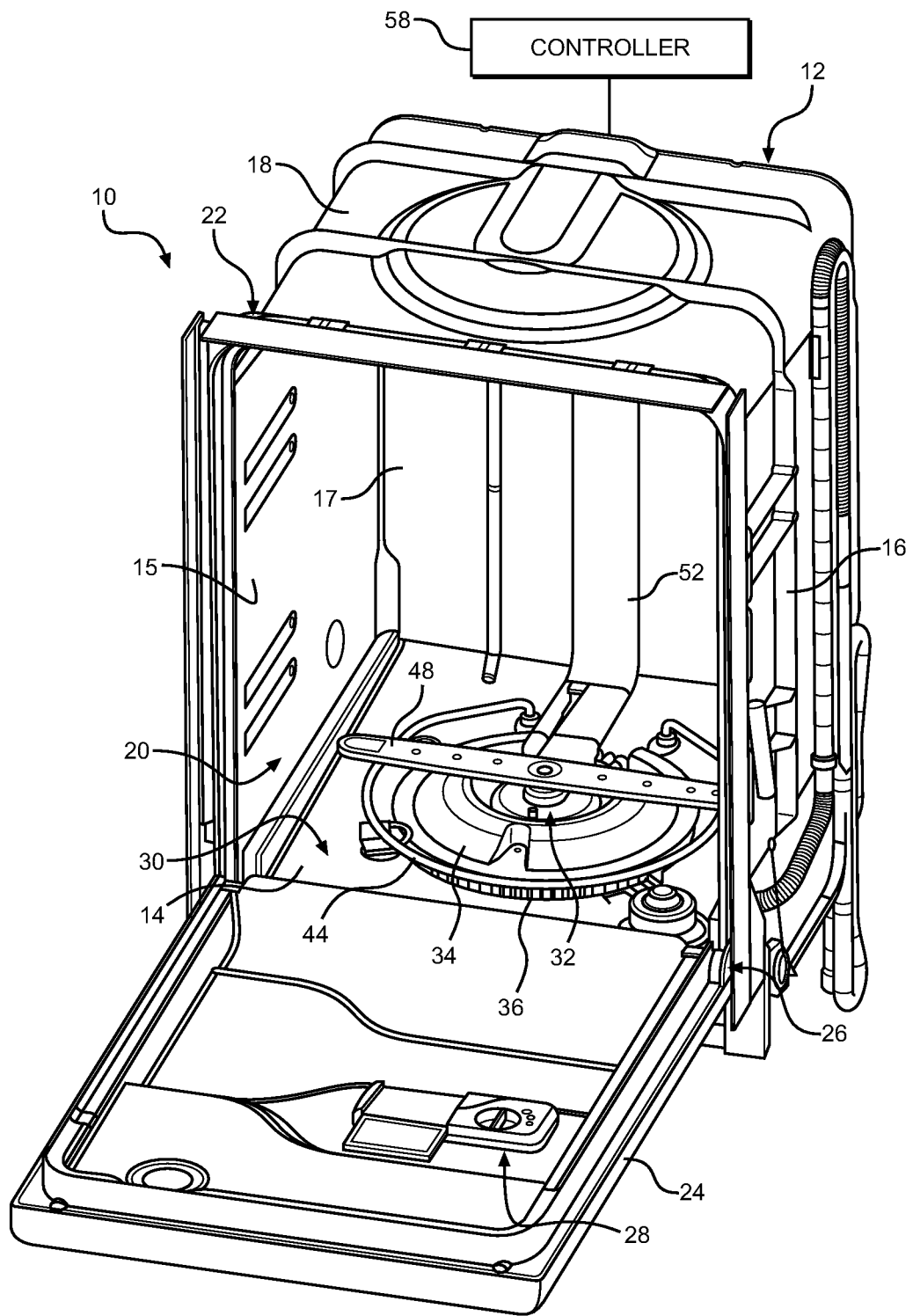
FIG. 1 is an upper right perspective view of a dishwasher utilized in conjunction with the present invention, with a door of the dishwasher being open.

With initial reference to FIG. 1, a dishwasher for use with the present invention is indicated at 10. As shown, dishwasher 10 includes a tub 12 which is preferably injection molded of plastic or formed of stainless steel so as to include integral bottom, side, rear and top walls 14-18 respectively. Within the confines of walls 14-18, tub 12 defines an interior 20 within which soiled kitchenware or dishware is adapted to be placed, such as upon shiftable upper and lower racks (not shown), with the kitchenware being cleaned during a washing operation in a manner widely known in the art. Tub 12 has attached thereto a frontal frame 22 which pivotally supports a door 24 used to create a seal during a washing operation. As shown, door 24 is pivotally supported to frame 22 at a bottom portion 26. In connection with the washing operation, door 24 is preferably provided with a detergent tray assembly 28 within which a consumer can place liquid or particulate washing detergent for dispensing at predetermined portions of the washing operation. Bottom, side and rear walls 14-17 of tub 12, as well as door 24 define a wash chamber indicated at 30 which is adapted to be filled with fluid for washing dishware.

Disposed within wash chamber 30 is a washing assembly generally indicated at 32. In the preferred embodiment and as illustrated in these figures, washing assembly 32 includes a main housing 34, and an annular, radial outermost strainer 36. Extending about a substantial portion of washing assembly 32, at a position raised above bottom wall 14, is a heating element 44. Heating element 44 preferably takes the form of a sheathed, electric resistance-type heating element. In a manner known in the art, washing assembly 32 is adapted to direct washing fluid to at least a lower wash arm 48 and a conduit 52, which leads to an upper spray arm (not shown). See, for example, U.S. Pat. No. 6,997,193, which is hereby incorporated by reference.

Figure 2:
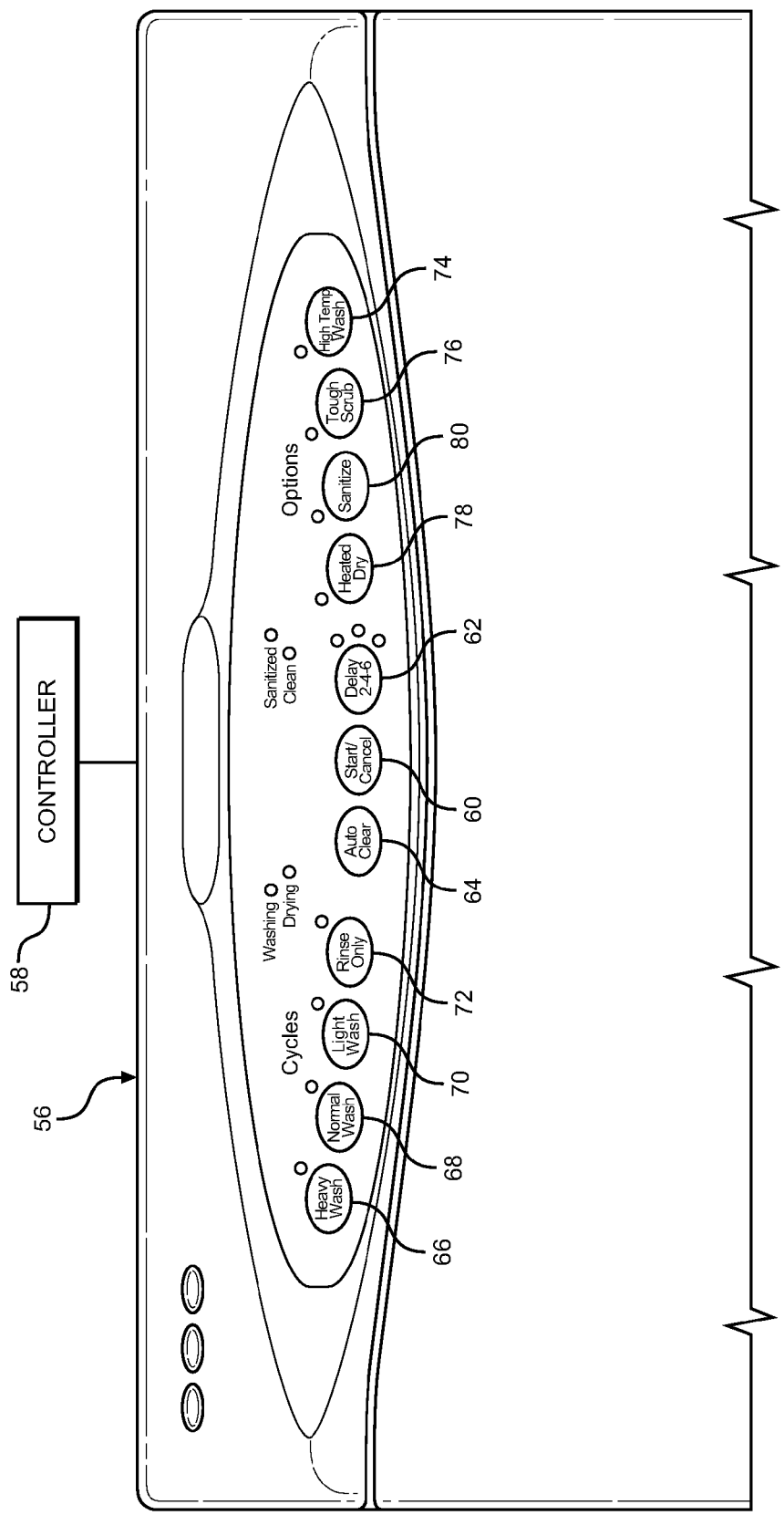
FIG. 2 is a front view of a control panel of the dishwasher of FIG. 1.

As depicted in FIG. 2, a control panel 56 for dishwasher 10 is linked to a controller 58 and provides a user with a variety of washing options. More specifically, control panel 56 preferably includes a start/cancel button 60, a delay programming button 62 and an auto clean button 64. Additionally, control panel 56 preferably includes a plurality of cycle options, such as heavy wash 66, normal wash 68, light wash 70 and rinse only 72, as well as washing options including high temperature wash 74, tough scrub 76 and heated dry 78. In accordance with the present invention, control panel 56 also includes a sanitize option 80 into which the steam purge operation of the invention is incorporated as will now be described in detail.

Figure 3:
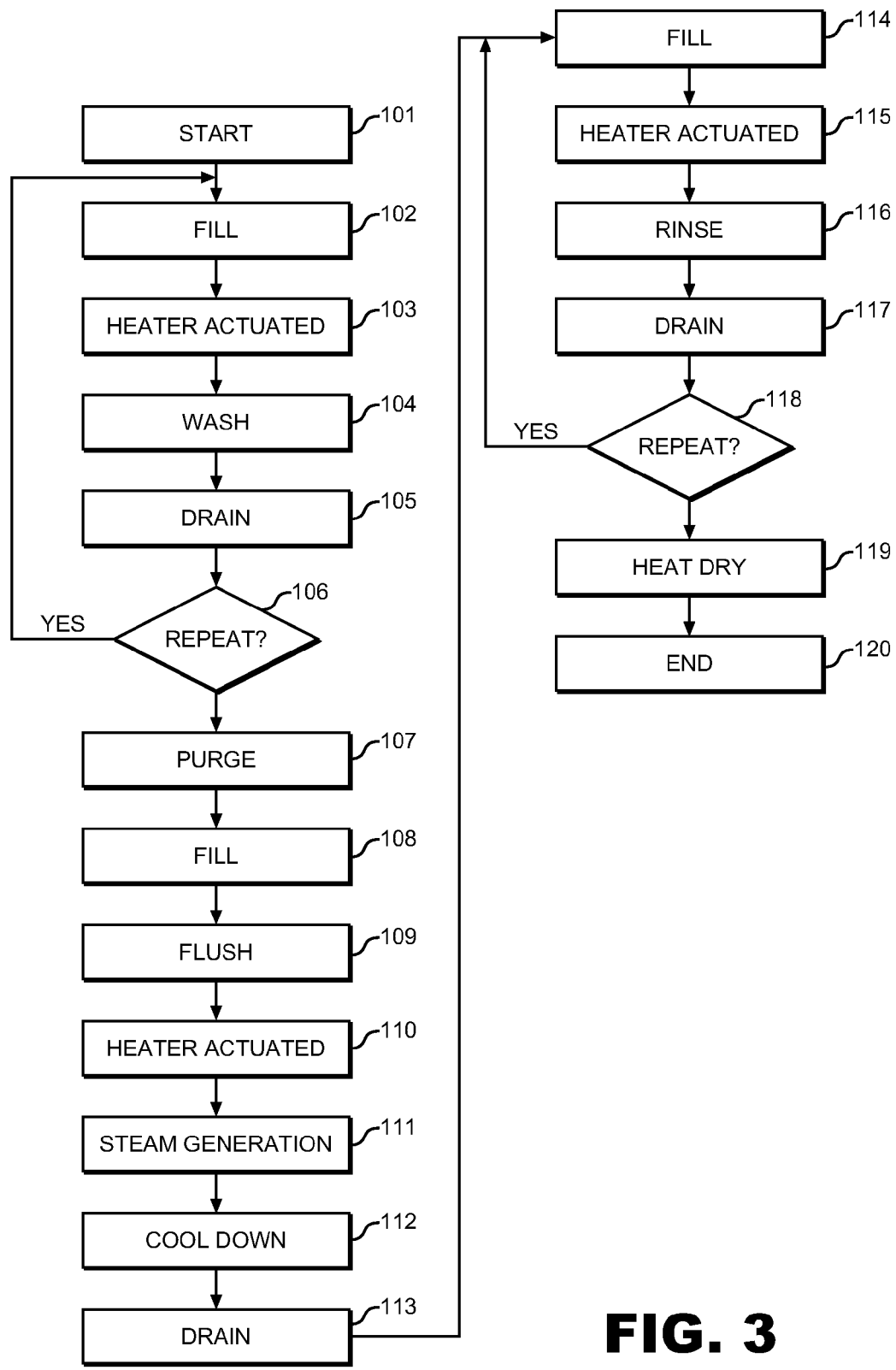
FIG. 3 is a flowchart illustrating the steam purge and sanitation method of the present invention.

With reference to FIG. 3, upon a user selecting a sanitize cycle through button 80 and pushing start/stop button 60 as indicated at 101, a washing cycle is performed wherein wash chamber 30 is initially filled with a washing fluid as indicated at step 102 to a level substantially at or preferably above heating element 44. The fluid is circulated and heated by activation of heating element 44 at step 103. When sanitize option 80 is selected, the fluid in wash chamber 30 is preferably heated to a disinfecting temperature of approximately 145° Fahrenheit (° F.). Washing assembly 32 is then activated and fluid from within tub 12 is distributed throughout wash chamber 30 by wash arm(s) 48 and conduit 52 in a manner known in the art to wash dishware within interior 20 as indicated at step 104. The washing fluid is then drained from wash chamber 30 at step 105. As indicated at step 106, steps 102-105 of the washing cycle can be repeated, such as based on the cycle options chosen by the consumer. For example, if heavy wash 66 is selected, steps 102-105 may be repeated two or three times. Next, a purge cycle 107 is initiated, wherein wash chamber 30 is filled with water to a level below heating element 44. In the preferred embodiment shown having a generally standard sized tub 12, approximately 2.4 liters of water is introduced at step 108. The water is then pumped through wash arm(s) 48 and conduit 52 to flush or purge dishwashing fluid from washing assembly 32 as indicated at step 109. Once this flushing or purging operation is complete, the pump associated with washing assembly 32 is deactivated and, at step 110, heating element 44 is activated through controller 58 for a predetermined period of time. Of course, the purge water, including the fresh water introduced at the being of the purge operation and the washing fluid mixed therewith after the purging, remains in tub 12, below the level of heating element 44. Therefore, the purge water from step 109, along with any remaining fluid in wash chamber 30, is heated by heating element 44 and converted to a high-temperature steam at step 111. Heating element 44 is then deactivated and allowed to cool for a period of time as indicated at step 112, before a drain step 113 commences to drain wash chamber 30.

Therefore, in accordance with the invention, the purge cycle starting at 107 is basically paused between steps 109 and 113 such that the steam generating portion of the cycle can be performed, with the steam generated in step 111 interacting with the dishware within interior 20 and loosens any remaining tough soil on the dishware. Although it is preferred to perform the purge operation with the introduction of water below the level of heating element 44, it is possible to provide more water and add a corresponding, partial drain step between flush step 109 and heater actuation step 110 to achieve the desired lower water level for steam generation purposes. In any case, after cool down step 112, a rinse cycle is then initiated, wherein wash chamber 30 is filled with water to a level substantially at or preferably above heating element 44 at step 114, heating element 44 is activated at step 115 to heat the rinse water, and then the rinse water is pumped through washing assembly 32 to rinse out interior 20 at step 116. When sanitize option 80 is selected, it is preferred to heat the rinse water to a disinfecting temperature of approximately 156° F. during step 115. A drain step 117 follows the rinsing operation. If desired, the rinse cycle indicated by steps 114-117 may be repeated as indicated at 118. With the sanitizing cycle, it is preferred that the heated dry option 78 is also automatically employed such that heating element 44 is activated to heat interior 20 and expedite drying of dishware therein at step 119 before the washing cycle ends at step 120.

Based on the above, it should be readily apparent that heating element 44 is advantageously utilized in accordance with the invention for each of the washing, rinsing and steam generating operations. Therefore, additional, dedicated steam generating components are not required. For this reason, dishwashers already on the market or in production may be readily programmed in accordance with the method described above and the invention can be implemented in an extremely cost effective manner. In addition, given that the steam generation utilizes fluid already employed in connection with a purge operation and only delays the drain at the end of the purge operation, steam generation can be added without any major modifications or substantial increase in overall cycle time.

Although described with reference to a preferred embodiments of the invention, it should be readily understood that various changes and/or modifications can be made to the invention without departing from the spirit thereof. For instance, although not discussed, the number of purge cycles prior to the steam cycle may be varied without departing from the invention. Additional, various pre-wash and pre-rinse cycles may be implemented prior to the washing cycle without departing from the invention. Furthermore, it should be recognized that a user option for steam generation could be directly added on control panel 56 such that the steam generation can be used in connection with other cycles including a purge operation. Finally, although the invention has been described for use in a more conventional dishwasher arrangement including a pivoting front door, the invention can be employed in a wide range of dishwashers, including drawer dishwashers. In general, the invention is only intended to be limited by the scope of the following claims.

What is claimed is:

1. A method of operating a dishwasher including a tub defining a wash chamber having a bottom wall, a door mounted for movement relative to the tub to selectively close the wash chamber, a heating element supported in the wash chamber above the bottom wall, and a washing assembly for supplying fluid to dishware placed within the wash chamber, the method comprising the steps of:

initiating a washing cycle including at least partially filling the tub with fluid, actuating the heating element to heat the fluid, spraying the heated fluid in the wash chamber through the washing assembly, and draining the tub of the fluid;

initiating a steam purge cycle including at least partially filling the tub with fluid and pumping the fluid through the washing assembly, actuating the heating element, with the fluid being below the heating element in the wash chamber, to heat fluid within the tub and generate steam within the wash chamber, deactivating the heating element, and draining the tub of fluid; and initiating a rinse cycle including filling the tub with fluid to a level substantially at or above the heating element, heating the fluid, rinsing the wash chamber with the heated fluid utilizing the washing assembly, and draining the tub.

2. The method of claim 1, further comprising, in the steam purge cycle, allowing the heating element to cool for a predetermined time period and draining the tub only after the predetermined time period has lapsed.

3. The method of claim 1 wherein, for the steam purge cycle, the tub is only filled to a level below the heating element in the wash chamber.

4. The method of claim 3 wherein, for the steam purge cycle, the tub is filled with approximately 2.4 liters of fluid.

5. The method of claim 1, further comprising: automatically performing the steam purge method in connection with a sanitize cycle of the dishwasher.

6. The method of claim 5, further comprising the step of initiating a heated dry cycle wherein the heating element is actuated to dry the dishware after draining of the fluid in the rinse cycle.

7. The method of claim 5, wherein the fluid is heated during the washing cycle to a temperature of at least 145° F.

8. The method of claim 7, wherein the fluid is heated during the rinse cycle to a temperature of at least 156° F.

9. A method of operating a dishwasher including a tub defining a wash chamber having a bottom wall, a door mounted for movement relative to the tub to selectively close the wash chamber, a heating element supported in the wash chamber above the bottom wall, and a washing assembly for supplying fluid to dishware placed within the wash chamber, the method comprising the steps of:

performing a washing cycle wherein washing fluid is sprayed within the wash chamber by operation of the washing assembly for cleaning the dishware;

initiating a purge cycle to cleanse the washing assembly of the washing fluid, pausing the purge cycle, performing a steam generating cycle and completing the purge cycle after the steam generating cycle is complete; and performing a rinse cycle wherein a rinse fluid is sprayed within the wash chamber by operation of the wash assembly.

10. The method of claim 9, wherein performing the washing cycle includes at least partially filling the tub with fluid, actuating the heating element to heat the fluid, spraying the heated fluid in the wash chamber through the washing assembly, and draining the tub of the fluid.

11. The method of claim 10 wherein performing the purge cycle includes at least partially filling the tub with fluid and pumping the fluid through the washing assembly and draining the tub of fluid, while performing the steam cycle includes actuating the heating element, with the fluid being below the heating element in the wash chamber, to heat fluid within the tub and generate steam within the wash chamber and subsequently deactivating the heating element.

12. The method of claim 11 wherein initiating the rinse cycle includes filling the tub with fluid to a level substantially at or above the heating element, heating the fluid, rinsing the wash chamber with the heated fluid utilizing the washing assembly, and draining the tub.

13. The method of claim 11, further comprising allowing the heating element to cool for a predetermined time period in the steam cycle and draining the tub in the purge cycle only after the predetermined time period has lapsed.

14. The method of claim 9 wherein, throughout the steam cycle, the tub is only filled to a level below the heating element in the wash chamber.

15. The method of claim 14 wherein, at a beginning of the steam cycle, the tub is filled with approximately 2.4 liters of fluid.

16. The method of claim 9, further comprising: automatically performing the steam cycle during the purge cycle in connection with a sanitize cycle of the dishwasher.

17. The method of claim 16, further comprising the step of initiating a heated dry cycle wherein the heating element is actuated to dry the dishware after draining of the fluid in the rinse cycle.

18. The method of claim 17, wherein the washing fluid is heated during the washing cycle to a temperature of at least 145° F.

19. The method of claim 18, wherein the rinse fluid is heated during the rinse cycle to a temperature of at least 156° F.

* * * * *